US006159712A

United States Patent [19]
Lau

[11] Patent Number: 6,159,712
[45] Date of Patent: Dec. 12, 2000

[54] METHODS FOR ENHANCING THE PRODUCTION OF INTERFERON IN CELL CULTURE

[75] Inventor: Allan S. Lau, San Francisco, Calif.

[73] Assignee: The Regents of the University of California, San Francisco, Calif.

[21] Appl. No.: 09/444,224

[22] Filed: Nov. 19, 1999

Related U.S. Application Data

[63] Continuation of application No. 08/701,136, Aug. 21, 1996.
[60] Provisional application No. 60/002,621, Aug. 22, 1995.

[51] Int. Cl.[7] .......................... C12P 21/02; C12N 15/19; C07K 14/56; C07K 14/565
[52] U.S. Cl. .................... 435/70.5; 435/69.51; 435/194; 435/360; 530/350
[58] Field of Search .............................. 435/70.5, 69.51, 435/194, 366; 530/350

[56] References Cited

U.S. PATENT DOCUMENTS

| | | |
|---|---|---|
| 4,469,790 | 9/1984 | Yamane et al. . |
| 4,485,038 | 11/1984 | Chadha et al. . |
| 4,548,900 | 10/1985 | Nobuhara . |
| 4,680,261 | 7/1987 | Nobuhara . |
| 4,732,683 | 3/1988 | Georgiades et al. . |
| 4,745,053 | 5/1988 | Mitsuhashi . |
| 4,780,413 | 10/1988 | Johnston . |
| 4,966,843 | 10/1990 | McCormick . |
| 5,149,531 | 9/1992 | Youngner et al. . |
| 5,196,323 | 3/1993 | Bodo . |
| 5,376,567 | 12/1994 | McCormick . |
| 5,525,513 | 6/1996 | Chen et al. . |

OTHER PUBLICATIONS

Antonelli et al., *J. Inf. Disease* (1991) 163:882–885.
Chong et al., *EMBO J.* (1992) 11:1553–1562.
D'Addario et al., *J. Virol.* (1990) 64:6080–6089.
Du et al., *Cell* (1993) 74:887–898.
Feng et al., *Proc. Natl. Acad. Sci. USA* (1992) 89:5447–5451.
Galabru et al., *J. Biol. Chem.* (1987) 262:15538–15544.
Green et al., *Genes & Development* (1992) 6:2478–2490.
Gutterman et al., *Natl. Acad Sci.* (1994) 91:1198–1205.
Henry et al., *J. Biol. Regulators and Homeostatic Agents* (1994) 8:15–24.
Hershey et al., *Ann. Rev. Biochem.* (1991) 60:717–755.
Jaramillo et al., *Cancer Investigation* (1995) 13:327–337.
Koromilas et al., *Science* (1992) 257:1685–1689.
Kumar et al., *Proc. Natl. Acad. Sci. USA* (1994) 91:6288–6292.
Lee et al., *Virol.* (1993) 193:1037–1041.
Maran et al., *Science* (1994) 265:789–792.
Marcus et al., *J. Gen. Virol.* (1988) 69:1637–45.
Matsuyama et al., *Cell* (1993) 75:83–97.
McCormack et al., *Virology* (1994) 198:92–99.
McMillan et al., *J. Biol. Chem.* (1995) 270:2601–2606.
Meurs et al., *Cell* (1990) 62:379–390.
Meurs et al., *Proc. Natl. Acad. Sci. USA* (1993) 90:232–236.
Meurs et al., *J. Virol.* (1992) 66:5805–5814.

Pestka et al., *Ann. Rev. Biochem.* (1987) 56:727–777.
Quesada et al., *J. Clin. Oncology* (1985) 3:1522–1528.
Sen et al., *J. Biol. Chem.* (1992) 267:5017–5020.
Tanaka et al., *Adv. Immunol.* (1992) 52:263–81.
Taylor et al., *Virus Research* (1990) 15:1–26.
Visvanathan et al., *EMBO J.* (1989) 8:1129–1138.
Williams et al., *Eur. J. Biochem.* (1991) 200:1–11.
Zinn et al., *Science* (1988) 240:210–3.
Der, S.D. and Lau, A.S., "Involvement of the double–stranded–RNA–dependent kinase PKR in interferon expression and interferon–mediated antiviral activity" *Proc. Natl. Acad. Sci. USA* 92:8841–8845 (1995).
Yang, Y.–L., et al., "Deficient signaling in mice devoid of double–stranded RNA–dependent protein kinase" *The EMBO J.* 14(24):6095–6106 (1995).
Enoch et al., Molecular Cell Biology, 6:801–810 (1986).
Havell et al., Antimicrobial, Agents and Chemotherapy, 2:6:476–484 (1972).
Lenardo et al., Cell 57:287–294 (1989).
Ringold et al., Proc. Natl'. Acad. Sci., 81:3964–3968 (1984).
Buffet–Janvresse et al., "Enhanced Level of Double–Stranded RNA–Dependent Protein Kinase in Peripheral Blood Mononuclear Cells of Patients with Viral Infections," Journal of Interferon Research, vol. 6:85–96 (1986).
Farrel P.J. et al., "Phosphorylation of Initiation Factor eIF–2 and the Control of Reticulocyte Protein Synthesis," Cell, vol. 11:187–200 (1977).
Hovanessian A.G., et al., "Double–stranded RNA dependent protein kinase (s) in rabbit reticulocyte lysated analogous to kinase from iterferon–treated cells," Biochimie, vol. 62:775–775 (1980).
Krust et al., "p67K Kinase in Different Tissues and Plasma of Control and Interferon–Treated Mice," Virology, vol. 120:240–246 (1982).
Lau A.S., "Downregulation of Interferon α but Not γ Receptor Expression In Vivo in the Acquired Immunodeficiency Syndrome," J. Clin. Invest., vol. 82:1415–1421 (1988).
Levin et al., "Regulation of protein synthesis: Activation by double–stranded RNA of a protein kinase that phosphorylates eukaryotic initiation factor 2," Proc. Natl. Acad. Sci. USA, vol. 75(3):1121–1125 (1978).
Barber et al., Proc. Natl. Acad. Sci. USA, (1994) 91:4278–4282.
Ozes et al., *J. Interferon Res.* (1994) 14:25–32.
Proud C.G., Trends Biochem. Sci. (TIBS), (1995) 20:6:241–246.
Thomas et al., *J. Immunol* (1993) 150:12:5529–5534.

*Primary Examiner*—Elizabeth Kemmerer
*Assistant Examiner*—David Romeo
*Attorney, Agent, or Firm*—Nina M. Ashton; Linda R. Judge; Peter J. Dehlinger

[57] ABSTRACT

Methods for enhancing the production of interferons in animal cell culture are described. These methods rely on the manipulation of the cellular levels of certain inducers of interferon production, in particular cellular levels of double-stranded-RNA-dependent kinase (dsRNA-PKR, or PKR). In cell cultures that overproduce PKR, interferon synthesis is induced to high levels, and significant amounts of interferon can be recovered without conventional induction of interferon by virus.

4 Claims, 3 Drawing Sheets

METHODS FOR ENHANCING THE PRODUCTION OF INTERFERON IN CELL CULTURE

This application is a continuation of U.S. application Ser. No. 08/701,136, filed Aug. 21, 1996, which claims the benefit of U.S. Provisional Application No. 60/002,621, filed Aug. 22, 1995.

TECHNICAL FIELD

The present invention relates to methods for enhancing the production of interferon in cell culture.

BACKGROUND

Interferons (IFNs) can be classified into two major groups based on their primary sequence. Type I interferons, IFN-α and IFN-β, are encoded by a super family of intronless genes consisting of the IFN-α gene family and a single IFN-β gene. Type II interferon, or IFN-γ, consists of only a single type and is restricted to lymphocytes (T-cells and natural killer cells). Type I interferons mediate diverse biological processes including induction of antiviral activities, regulation of cellular growth and differentiation, and modulation of immune functions (Sen, G. C. & Lengyel, P. (1992) *J. Biol. Chem.* 267, 5017–5020; Pestka, S. & Langer, J. A. (1987) *Ann. Rev. Biochem.* 56, 727–777). The induced expression of Type I IFNs, which include the IFN-α and IFN-β gene families, is detected typically following viral infections. Many studies have identified promoter elements and transcription factors involved in regulating the expression of Type I IFNs (Du, W., Thanos, D. & Maniatis, T. (1993) Cell 74, 887–898; Matsuyama, T., Kimura, T., Kitagawa, M., Pfeffer, K., Kawakami, T., Watanabe, N., Kundig, T. M., Amakawa, R., Kishihara, K., Wakeham, A., Potter, J., Furlonger, C. L., Narendran, A., Suzuki, H., Ohashi, P. S., Paige, C. J., Taniguchi, T. & Mak, T. W. (1993) Cell 75, 83–97; Tanaka, N. & Taniguchi, T. (1992) *Adv. Immunol.* 52, 263–81). However, it remains unclear what are the biochemical cues that signify viral infections to the cell and the signaling mechanisms involved (for a recent review of the interferon system, see Jaramillo et al. Cancer Investigation 1995 13:327–337).

IFNs belong to a class of negative growth factors having the ability to inhibit growth of a wide variety of cells with both normal and transformed phenotypes. IFN therapy has been shown to be beneficial in the treatment of human malignancies such as Kaposi's sarcoma, chronic myelogenous leukemia, non-Hodgkin's lymphoma and hairy cell leukemia as well as the treatment of infectious diseases such as papilloma virus (genital warts) and hepatitis B and C (reviewed by Gutterman Proc. Natl Acad Sci. 91:1198–1205 1994). Recently genetically engineered, bacterially produced IFN-β was approved for treatment of multiple sclerosis, a relatively common neurological disease affecting at least 250,000 patients in the United States alone.

Currently, IFNs for therapeutic use are produced from two major sources, natural IFNs from human leukocytes or leukocyte cell lines and recombinant IFNs produced in bacterial cells. Natural IFNs are considered to be superior as they consist of the entire complement of IFNs and have the proper structure, but they are expensive and time-consuming to produce. Bacterially produced recombinant IFN is cheaper and more efficient to make, but studies have shown much higher rates of rejection for the bacterially produced protein, particularly after long term usage. For instance, previous medical studies have shown that the incidence of rejection as reflected by antibody formation can be as high as 20 to 38% for bacterially-produced IFN compared with only 1.2% for natural IFN-α (Antonelli et al. J. Inf. Disease 163:882–885 1991; Quesada et al. J. Clin. Oncology 3:1522–1528 1985). Thus, a method for enhancing the production of natural IFN to make it less expensive to produce would be advantageous.

IFNs elicit their biological activities by binding to their cognate receptors followed by signal transduction leading to induction of IFN-stimulated genes (ISGs). Some ISGs have been characterized and their biological activities examined. The best studied examples of ISGs include a double-stranded-RNA-dependent kinase (dsRNA-PKR, or just PKR, formerly known as p68 kinase), 2'-5'-linked oligoadenylate (2-5A) synthetase, and Mx proteins (Taylor JL, Grossberg SE. Virus Research 1990 15:1–26.; Williams BRG. Eur. J. Biochem. 1991 200:1–11.).

PKR (short for protein kinase, RNA-dependent) is the only identified dsRNA-binding protein known to possess a kinase activity. PKR is a serine/threonine kinase whose enzymatic activation requires dsRNA binding and consequent autophosphorylation (Galabru, J. & Hovanessian, A. (1987) J. Biol. Chem. 262, 15538–15544; Meurs, E., Chong, K., Galabru, J., Thomas, N. S., Kerr, I. M., Williams, B. R. G. & Hovanessian, A. G. (1990) Cell 62, 379–390). PKR has also been referred to in the literature as dsRNA-activated protein kinase, P1/eIF2 kinase, DAI or dsI (for dsRNA-activated inhibitor), and p68 (human) or p65 (murine) kinase. Analogous enzymes have been described in rabbit reticulocytes, different murine tissues, and human peripheral blood mononuclear cells (Farrel et al. (1977) Cell 11, 187–200; Levin et al. (1978) *Proc. Natl Acad. Sci. USA* 75, 1121–1125; Hovanessian (1980) *Biochimie* 62, 775–778; Krust et al. (1982) Virology 120, 240–246; Buffet-Janvresse et al. (1986) *J. Interferon Res.* 6, 85–96). The best characterized in vivo substrate of PKR is the alpha subunit of eukaryotic initiation factor-2 (eIF-2a) which, once phosphorylated, leads ultimately to inhibition of cellular and viral protein synthesis (Hershey, J. W. B. (1991) *Ann. Rev. Biochem.* 60, 717–755). This particular function of PKR has been suggested as one of the mechanisms responsible for mediating the antiviral and antiproliferative activities of IFN-α and IFN-β. An additional biological function for PKR is its putative role as a signal transducer. Kumar et al. demonstrated that PKR can phosphorylate IκBα, resulting in the release and activation of nuclear factor κB (NF-κB) (Kumar, A., Haque, J., Lacoste, J., Hiscott, J. & Williams, B. R. G. (1994) *Proc. Natl. Acad. Sci. USA* 91, 6288–6292). Given the well-characterized NF-κB site in the IFN-β promoter, this may represent a mechanism through which PKR mediates dsRNA activation of IFN-β transcription (Visvanathan, K. V. & Goodbourne, S. (1989) *EMBO J.* 8, 1129–1138).

The present inventor have surprisingly discovered that manipulating the expression of certain ISGs can have beneficial uses in interferon production. They have discovered that over-expression of the PKR protein induces overproduction of the IFN-α and IFN-β interferons, which is useful for the enhanced production of interferon in animal cell culture.

Relevant Literature

Currently there are two major approaches to large-scale production of interferons: recombinant IFN produced in bacterial or mammalian cells or natural IFNs from human leukocyte cells following stimulation with viruses or other IFN inducers. U.S. Pat. No. 5,376,567 and U.S. Pat. No. 4,966,843 describe the production in Chinese hamster ovary cells of a recombinant human interferon; U.S. Pat. No. 5,196,323 describes the production of recombinant human IFN-α in *E. coli* cells. A number of patents describe the production of interferon from human leukocyte cells using a variety of protocols; for example, U.S. Pat. No. 4,745,053 describes a process for producing interferon from whole human blood using a viral inducer, U.S. Pat. No. 4,680,261 describes a process for inducing production of interferon in mammalian cell culture using an ascorbic acid derivative or an inorganic vanadium compound, and U.S. Pat. No. 4,548,900 describes a process for the induction of interferon using a polyhydric alcohol in a priming stage. The major disadvantage of the current methods of interferon production is that typically virus is used as the IFN inducer because other inducers do not produce high enough levels of interferon for most commercial purposes. The virus must then be removed from the interferon before use, which adds time and cost to the production method. In addition, use of virus as an inducer ultimately results in the death of the interferon-producing cells, so that no recycling and re-use of the cells is possible.

The present invention overcomes these problems by providing a interferon-production system that does not require the use of a viral inducer in order to achieve high levels of interferon production. Although viral inducers can be used with the systems of the invention, other inducers that do require removal prior to use of the IFNs are still capable of producing IFNs at commercially acceptable levels.

SUMMARY OF THE INVENTION

It is an object of this invention to provide a method for enhancing the production of interferon in animal cell culture without requiring the addition of virus as an inducer.

This object is generally accomplished by providing animal cell cultures in which the expression of the interferon genes is substantially increased from the normal level of expression. This may be effected by manipulating the level of expression of factors that function in vivo to regulate the interferon level, including interferon transcriptional regulators (for example, IRF1), interferon receptors, and interferon stimulated gene products (for example PKR and 2-5A synthetase).

Thus, increased production of INF and other objects of the invention as will hereinafter become apparent are accomplished by carrying out interferon production in animal cell cultures in which the level of interferon-regulating protein activity, particularly for double-stranded-RNA-dependent kinase (PKR) and 2'-5' oligoadenylate synthetase (2-5A synthetase), is significantly increased from normal levels.

DESCRIPTION OF SPECIFIC EMBODIMENTS

Figure 1A:
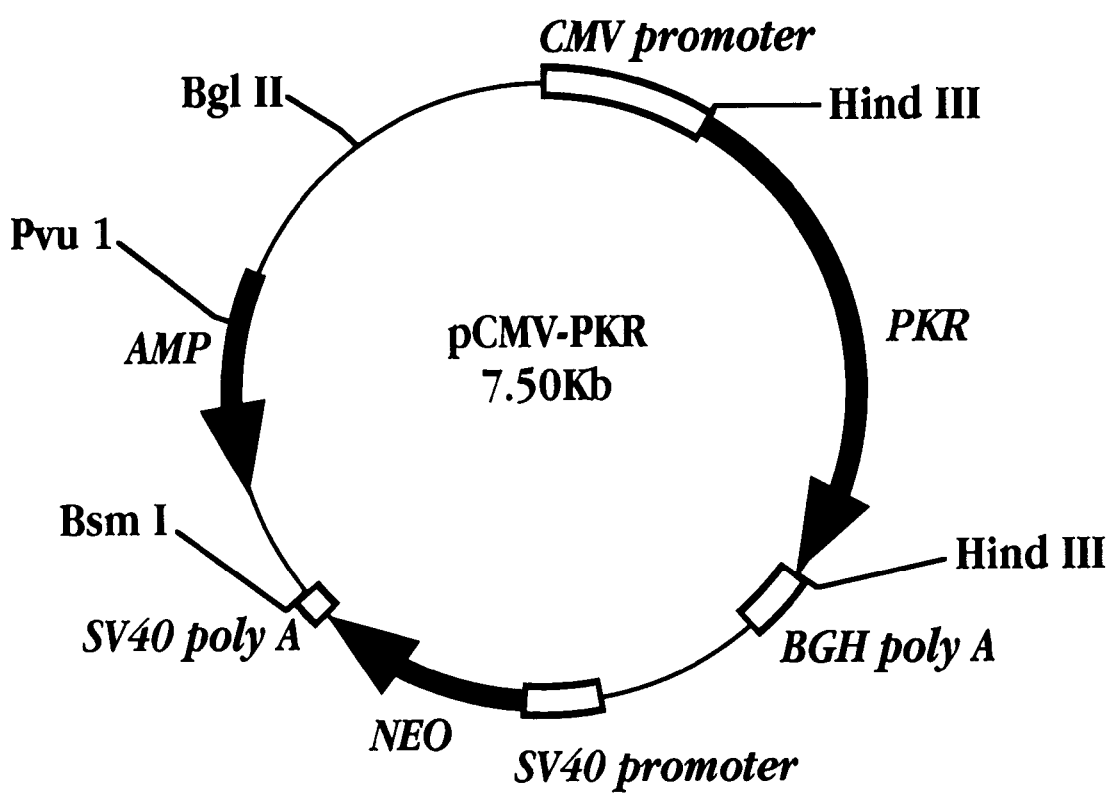
FIG. 1. Diagrammatic drawings of pCMV-PKR and pMT-PKR. 1(A) Diagram of the pCMV-PKR showing the human PKR cDNA in the sense orientation driven by the promoter sequence from the immediate early gene of human cytomegalovirus. 1(B) Diagram of the pMT-PKR showing the human PKR cDNA in the sense orientation driven by the cadmium inducible metallothionein II promoter.

The present invention arose in part from the discovery by the inventor that the level of interferon production in cell culture can be regulated by control of the expression or activity of certain proteins that normally regulate interferon expression in vivo. These factors include interferon-specific transcriptional regulators (particularly IRF1), interferon receptors, and the gene products of certain interferon simulated genes (also called interferon-mediated antiviral responses), particularly PKR. Enhancing the expression or activity of any of these factors will result in a higher than normal level of expression of interferon genes. One result of this higher than normal expression of interferon genes is that interferon production can be achieved with greater efficiency and lower cost. The remainder of this specification will be exemplified by reference to PKR, but it is to be understood that other interferon enhancing factors as described herein can be used in place of PKR.

By increasing the level of PKR protein (and therefore PKR activity) in an animal cell, interferon production can be increased. Animal cell cultures which express a higher constitutive level of PKR or in which PKR expression can be induced to higher levels are therefore useful for the production of interferons. Problems typically associated with production of interferons in cell culture, for example low yield and contamination with the virus used to induce interferon expression, are eliminated in the method of the present invention. Thus, a high yield of interferon protein can be achieved without the need for induction with virus (although virus can be used for even higher INF production).

The method relies on the use of PKR-overproducing cells as the source of the interferon, but any known or later-discovered method of interferon production may be used. No particular method of production of interferon is required except that typically a non-viral interferon inducer is used. In particular, the method comprises (a) culturing an animal cell culture capable of overproduction of PKR or an analog or homolog of PKR under conditions sufficient to overproduce PKR, and (b) treating the cell culture as appropriate to induce the expression of the interferon genes, particularly the IFN-β and IFN-α. These steps are generally followed by purifying the interferon produced. In some cases, the overproduction is not of PKR itself, but of an analog of PKR, by which is meant a non-natural protein kinase that can mediate dsRNA activation of interferon transcription (usually obtained by genetic manipulation of the gene encoding a particular PKR from a selected animal cell line). The cell culture used to produce interferon can overproduce PKR from any animal cell line used to produce the interferon, such as the PKR normally found in rabbit reticulocytes, various mouse tissues, or human peripheral blood mononuclear cells. Usually, the natural PKR for a particular cell line (as opposed to an exogenous PKR) is used for overexpression. Preferably murine p65 kinase and most preferably human p68 kinase is overproduced, in a corresponding murine or human cell culture, respectively.

Animal cell cultures capable of overproduction of a PKR gene may be isolated by any number of methods, including many that are well known in the art. Such methods include selection for cells expressing higher PKR levels, transfection with a vector containing a PKR gene (or cDNA) under control of a constitutive promoter (for example, a CMV, RSV or SV40 promoter), or transfection with a vector containing a PKR gene or cDNA under the control of an inducible promoter (for example, a heat shock promoter, a metallothionein promoter or a glucocorticoid promoter). Transfection is carried out as described previously and transfectants are selected for overproduction of PKR. By overproduction of PKR is meant higher than normal levels of PKR activity. Normal refers to under normal conditions for the cell line being used (see, for example, suggested culture conditions as supplied in catalogues for commercial cells, especially the ATCC Catalogue of Strains, available from the American Type Culture Collection, Rockville, Md., USA, or in scientific publications describing the cell line being used, if it is not commercially available), and in various preferred embodiments refers to production of INF under otherwise identical conditions in the parental cell line from which a production cell line is selected or produced by genetic engineering. Higher than normal level preferably means at least 150%, more preferably at least 200 or 300%, most preferably at least 500%, of normal PKR level. The PKR-overproducing cell culture may be constitutive for PKR overproduction or inducible for PKR overproduction, depending on the particular method used to isolate or prepare the culture. Preferably the PKR-overproducing cell culture will be inducible for PKR overproduction in order to regulate the level of PKR available for IFN induction. It will be apparent that if the PKR-overproducing cell culture is inducible for overproduction, PKR activity for overproduction will be assayed under inducing conditions. PKR activity can be determined by any of the methods known in the art or described in the following examples.

Any of a number of known cell cultures are useful as a parental strain for making a PKR-overproducing cell culture. Any cells normally capable of producing interferon are suitable as the parental strain, particularly cells derived from fibroblasts or immune cells, including B cells and monocytes. Particularly suitable cell cultures are pro-monocytic U937 cells, Namalwa (lymphoblastoid B) cells and MRC-5 (human fibroblast) cells. Also suitable are WI-38 cells, Flow 1000 cells, Flow 4000 cells, FS4 and FS-7 cells, MG-63 cells, CCRF-SB cells and CCRF-CEM cells.

Production of interferon in the PKR-overproducing cell culture is accomplished by methods that are well known in the art. Generally, the interferon producing cells are cultured in any suitable medium, treated with an inducer to induce expression of the interferons (and with an inducer of the PKR gene, in PKR is provided under the control of an inducible promotor), and incubated following induction of interferon production. The interferon is then isolated. The cells may be primed prior to induction by addition of a priming agent. Interferon inducers are many and well -known in the art and almost any known interferon inducer can be used in the present invention. Typical inducers include poly(I):poly(C), Sendai virus, Newcastle disease virus, concanavaline A, chlamydia, rickettsia, mitogen, and lipopolysaccharides. Preferably, the inducer will be a non-viral inducer. More preferably, the inducer will be poly(I):poly(C) or poly r(I):poly r(C). Non-viral inducers are preferred because the cells do not suffer the deleterious consequences that exposure to the virus provides and may therefore be recycled for re-use resulting in a lower cost of production. Typical priming agents include phorbol myristate acetate, calcium ionophores and interferons.

IFNs are purified by standard techniques that are well known in the art. These include antibody-affinity column chromatography, ion exchange chromatography, protein precipitation and centrifugation (U.S. Pat. No. 5,391,713); chromatography using CM-agarose, con A-agarose, and phenyl-agarose (U.S. Pat. No. 4,658,017); three step chromatography with glass sorbent column (U.S. Pat. No. 4,732,683); immunoaffinity chromatography, reverse phase HPLC, cation exchange column, and gel filtration (U.S. Pat. No. 4,765,903); guanidine HCl as solvent and HIC column chromatography (U.S. Pat. No. 4,845,032).

The levels of IFN-α in the preparations can be determined by titrating for antiviral activity on L929 (murine fibroblast) cells against National Institute of Allergy and Infectious Diseases reference standard G-023-901-527 (Lau et al. J. Clin. Invest. 82:1415–1421 1988). In this technique, $5 \times 10^4$ L929 cells are seeded into each well of 96-well microtiter plates and then incubated with two-fold serial dilutions of culture supernatants for 16 hr. The cells are subsequently challenged with EMCV or Sendai virus (0.1 or 0.01 TCID per cell). Virus-induced cytopathic effects were assessed by microscopic examination and by staining cells with 0.1% crystal violet in 5% ethanol solutions. The IFN titer is defined as the reciprocal of the highest dilution of culture supernatants capable of protecting 50% of the cells from viral-induced cytopathic effects.

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLES

Example 1: Preparation of Constitutive PKR Overexpressing Cell Culture

Plasmid pCMV-PKR was prepared from pRC/CMV by inserting the PKR cDNA from pBS-8.6R into the HindIII site of the pRC/CMV vector so that expression of the PKR coding sequence is under control of the CMV promoter. The pRC/CMV plasmid (Invitrogen) is commonly used for eukaryotic expression. The vector offers the following features suitable for PKR transcription: i) promoter sequences from the immediate early gene of the human CMV (cytomegalovirus) for high level transcription; ii) polyadenylation signal and transcription termination sequences from bovine growth hormone (BGH) gene to enhance RNA stability; iii) SV40 origin for episomal replication and simple vector rescue; iv) T7 and Sp6 RNA promoters flanking the multiple cloning site for in vitro transcription of sense and antisense RNA; and v) the ampicillin resistance gene (AMP) and ColE1 origin for selection and maintenance in E. coli. The vector also contains a G418 resistance marker (NEO) to allow for selection and identification of the plasmids after transfer to eukaryotic cells. The structure of pCMV-PKR is shown in FIG. 1A.

Stable transfectants were obtained by electroporation of $5 \times 10^6$ exponentially growing U937 cells with 10 mg of each plasmid, in serum-free RPMI-1640 containing DEAE-dextran (50 mg/mL), with a Gene Pulser apparatus (BioRad) set at 500 μF, 250V. Bulk populations of stable transfectants were obtained by selection with 400 μg/mL geneticin (GIBCO-BRL) for 3 weeks. Clonal lines were subsequently obtained by limiting dilution cloning. Cell lines were cultured in RPMI-1640 containing 10% fetal calf serum (complete media) and geneticin. One representative transfectant cell line was selected and designated "U937-PKR+". The level of PKR produced in U937-PKR+ was analyzed and found to be increased approximately five-fold over normal (parental) levels. As a control, U937 cells were transfected with pRC/CMV and a representative transfectant cell line was isolated and designated "U937-neo". The transfectant cell lines were tested for IFN production in the presence or absence of priming agents and/or inducers.

U937-PKR+ cells and U937-neo cells were cultured in RPMI 1640 medium, supplemented with fetal bovine serum. The cells were pretreated with or without phorbol myristate acetate (PMA) (10nM) for 20 hr and with or without subsequent stimulation by poly r(I):r(C), 10 ug/ml, for 20 hr. Twenty-four hr after the stimulation with poly r(I):r(C), culture supernatants were collected for IFN assays.

Figure 2:
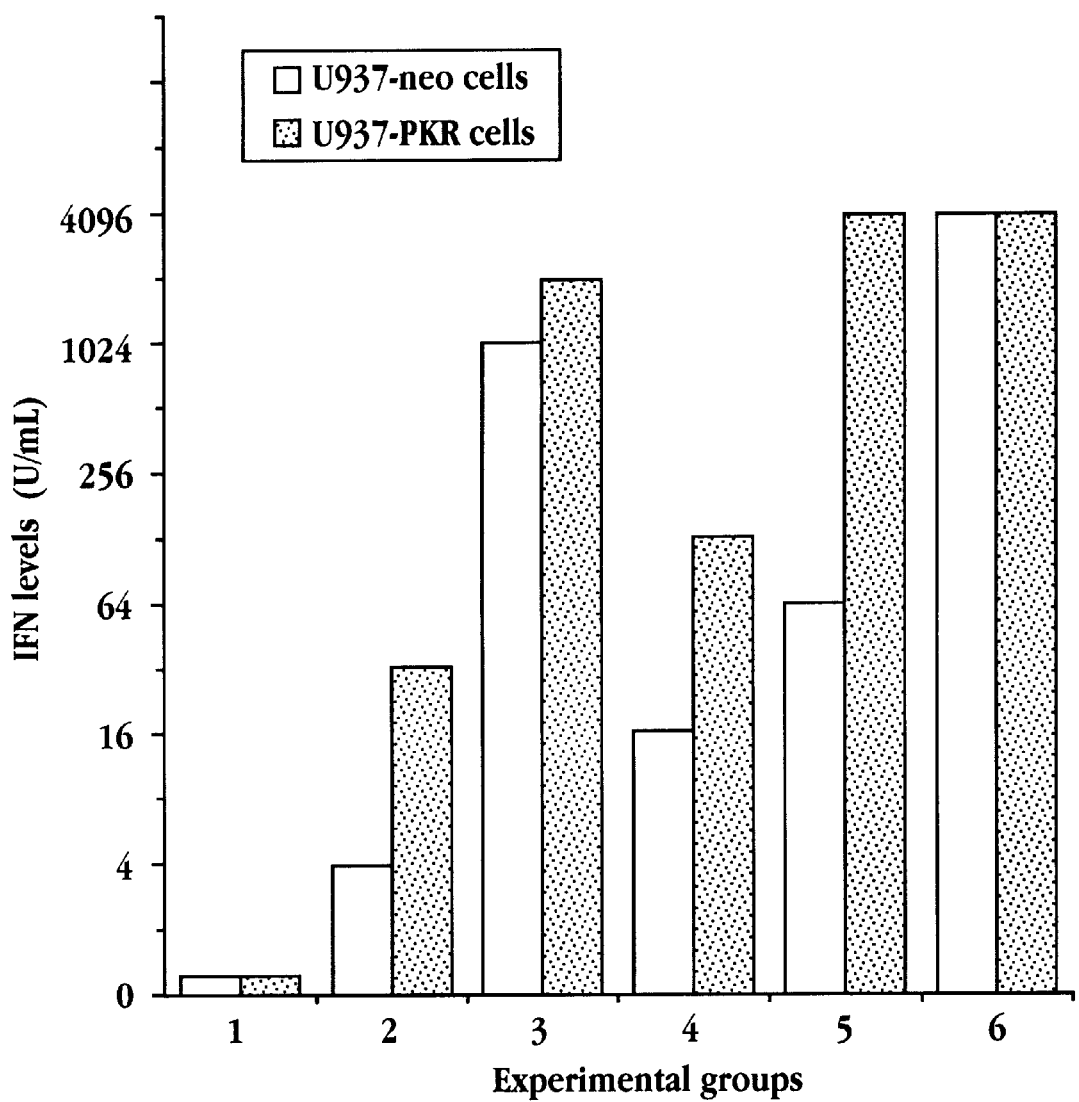
FIG. 2. Interferon induction in U937-PKR+ cells and control U937-neo cells. U937-PKR+ cells and U937-neo cells ($0.5 \times 10^6$/ml) were cultured in RPMI 1640 medium, supplemented with 5% fetal bovine serum. The cells were pretreated ("primed") with or without 10 nM PMA for 20 hrs followed by induction with 10 μg/ml poly r(I):poly r(C) or with 0.1 $TCID_{50}$/ cell EMCV for 20 hrs. Twenty-four hours after induction, culture supernatants were collected and assayed for IFN-α. The open bars indicate U937-neo cells, the hatched bars indicate U937-PKR+ cells. The experimental groups indicate different treatments: 1- no treatment; 2- poly r(I):poly r(C) induction alone; 3- EMCV induction alone; 4- PMA priming alone; 5- PMA priming and poly r(I):poly r(C) induction; 6- PMA priming and EMCV induction.

As shown in FIG. 2, neither transfectant cell line produced IFN spontaneously in the absence of priming agents or inducers. In response to poly r(I):poly r(C), control U937-neo cells showed minimal synthesis of IFN-$\alpha$ either with or without PMA priming (open bar 2 and 5). In contrast, U937-PKR+ cells showed increased IFN production in response to poly r(I):poly r(C) induction, with or without PMA priming, reaching a level of 4000 U/ml when treated with both poly r(I):poly r(C) and PMA (hatched bars 2 and 5). In the absence of PMA priming, EMCV induced high levels of IFN in both transfectant cell lines (more than 1000 U/ml), with slightly higher levels in the U937-PKR+cells (Bar 3). In the absence of EMCV or poly r(I):poly r(C) inducer, U937-PKR+ cells produced higher levels of IFNs than did U937-neo cells in response to PMA priming alone (Bar 4). With PMA priming and EMCV induction, both transfectant cell lines produced more than 4000 U/ml IFN (Bar 6). Taken together, these results indicated that following priming with PMA, the U937-PKR+ cells are as efficient in IFN production when poly r(I):poly r(C) is used as inducer as are control cells when virus is used as inducer. Therefore the use of live virus for IFN production can be eliminated when PKR-overproducing cells are used.

Following induction by poly r(I):poly r(C), the U937-PKR+ cells were examined for viability using a trypan blue exclusion assay. We found that more than 95% of the cells were viable. In contrast, the use of EMCV as an inducer resulted in the death of all of the cells. Thus, the U937-PKR+ cells can be recycled for continuous production of IFN.

Example 2: Preparation of Inducible PKR Overexpressing Cell Culture

Figure 1B:
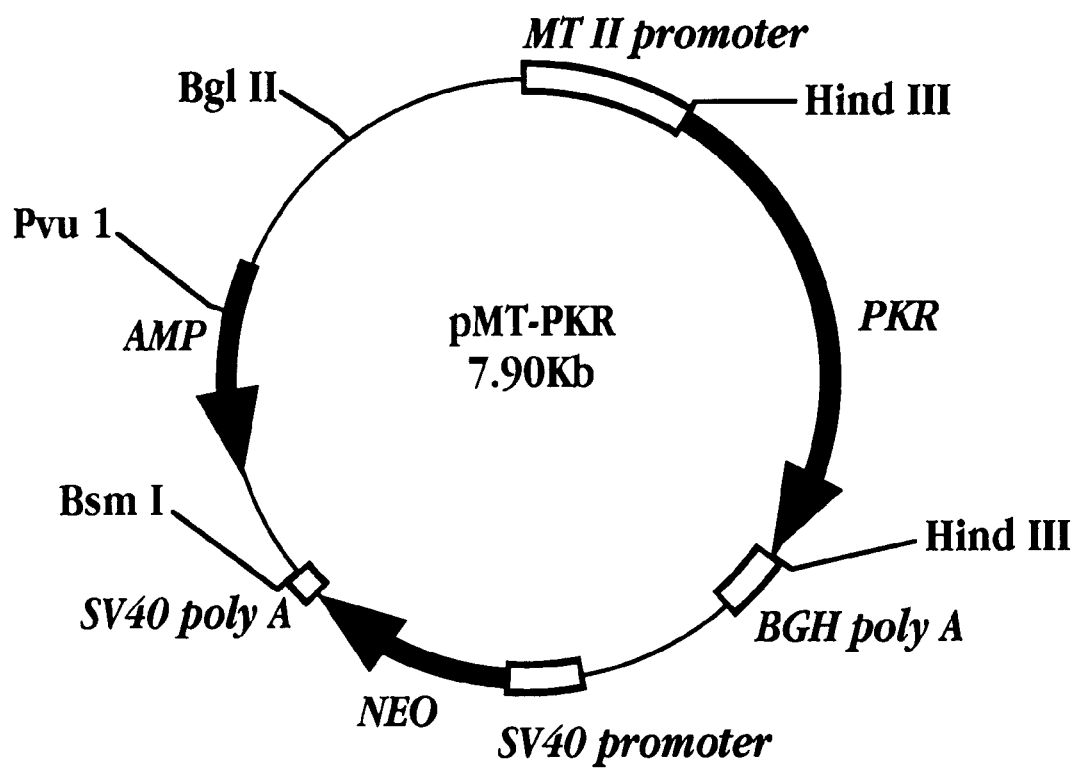

Plasmid pMT-PKR was made by replacing the CMV promoter upstream from the PKR cloning site in pCMV-PKR with a cadmium-inducible metallothionein II promoter (Hewison et al. J. Immunol. 153:5709–5719 1994). The structure of pMT-PKR is shown in FIG. 1B. Stable transfectants of pMT-PKR into U937 cells were isolated as described in Example 1 for pCMV-PKR transfectants. The MTII promoter is inducible by zinc or cadmium ions. PKR activity levels in the transfectants were measured after induction of the transfected PKR gene by addition of 20 $\mu$M cadmium chloride.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the described invention.

What is claimed is:

1. A method for producing $\alpha$- or $\beta$-interferon in a human cell culture, in the absence of viral induction, comprising:

(a) culturing a human cell line capable of producing interferon and transfected with a vector containing DNA encoding duble-stranded-RNA-dependent kinase PKR under the control of a promoter, under culture conditions in which PKR is overproduced in the transfected cells, as evidenced by levels of PKR in said transfected cell line which are higher than those obtained in said human cell line which is not transfected with said vector, when grown under the same culture conditions, (b) treating said cultured, PKR-overproducing human cell line with double-stranded RNA (dsRNA), in the absence of viral induction, and (c) collecting $\alpha$- or $\beta$-interferon produced by the cultured, treated cell line.

2. The method of claim 1, wherein said culturing includes priming the cells with phorbal myristate acetate (PMA).

3. The method of claim 1, wherein said collecting includes isolating $\alpha$-interferon produced by the cultured, treated cells.

4. The method of claim 1, wherein said collecting includes isolating $\beta$-interferon produced by the cultured, treated cells.

* * * * *

UNITED STATES PATENT AND TRADEMARK OFFICE
CERTIFICATE OF CORRECTION

PATENT NO. : 6,159,712
DATED : December 12, 2000
INVENTOR(S) : Lau

It is certified that error appears in the above-identified patent and that said Letters Patent is hereby corrected as shown below:

<u>Claim 1,</u>
Line 5, change "duble" to -- double --; and
Line 6, change "PKR" to -- (PKR) --

Signed and Sealed this

Fifth Day of February, 2002

*Attest:*

JAMES E. ROGAN
*Attesting Officer*     *Director of the United States Patent and Trademark Office*